US00PP34294P2

(12) United States Plant Patent
Pruitt

(10) Patent No.: US PP34,294 P2
(45) Date of Patent: Jun. 7, 2022

(54) SUGAR MAPLE TREE NAMED 'GALLATIN'

(50) Latin Name: *Acer saccharum*
Varietal Denomination: Gallatin

(71) Applicant: Aaron D. Pruitt, Bozeman, MT (US)

(72) Inventor: Aaron D. Pruitt, Bozeman, MT (US)

( * ) Notice: Subject to any disclaimer, the term of this patent is extended or adjusted under 35 U.S.C. 154(b) by 0 days.

(21) Appl. No.: 17/300,422

(22) Filed: Jun. 28, 2021

(51) Int. Cl.
*A01H 5/12* (2018.01)
*A01H 6/00* (2018.01)

(52) U.S. Cl.
USPC ..... Plt./224
CPC ..... *A01H 6/00* (2018.05)

(58) Field of Classification Search
USPC ..... Plt./224
CPC ..... A01H 6/00
See application file for complete search history.

*Primary Examiner* — Anne Marie Grunberg
(74) *Attorney, Agent, or Firm* — Lewis Roca Rothgerber Christie LLP

(57) ABSTRACT

A new and distinct variety of sugar maple tree having early dormancy and winter hardiness for high altitude, short growing season climates, its upright and rounded form and as to its consistent and striking red fall foliage.

5 Drawing Sheets

Classification:
Genus and species: *Acer saccharum.*
Variety denomination: 'Gallatin'.

BACKGROUND OF THE INVENTION

The present invention relates to a new and distinct variety of sugar maple tree grown in Bozeman, Mont.

SUMMARY OF THE INVENTION

This new sugar maple cultivar is a selection from a block of seedlings I propagated by seed collected from mature trees in the Sunset Hills Cemetery of Bozeman, Mont. in 1992. By this tree's fifth year, I observed distinct hardiness and fall color characteristics which set it apart from other sugar maples growing in my private, non-commercial, hobby nursery. I transplanted the tree in 1997 to its permanent location in my farm pasture, where over the next 29 years it has flourished eight miles west of Bozeman, Mont. This cultivar consistently enters dormancy one to two weeks earlier in the fall than my other seed propagated sugar maples, and approximately three to four weeks before the 'Green Mountain' sugar maple cultivar also growing on my farm. At 4,800 feet in elevation, Bozeman sits in a high Rocky Mountain valley. In addition to a very short growing season, the region is regularly subject to dramatic and rapid temperature swings. Many tree species in the Bozeman area, including sugar maples, periodically exhibit mild to severe winter dieback resulting from early October freezes. My sugar maple's early dormancy trait protects it from frost with little to no tissue damage. In addition to exceptional cold hardiness, the tree exhibits a consistently brilliant red fall leaf color, deeper in saturation and more intense than the common sugar maple.

This new *Acer saccharum* cultivar exhibits the following combination of characteristics:

(a) Better winter hardiness in short growing season, high altitude locations than the typical Sugar Maple.
(b) Consistent, uniform and brilliant red fall leaf coloring.

(c) Vigorous growth in youth.
(d) Dense foliage with upright, rounded form.

DETAILED BOTANICAL DESCRIPTION

Figure 1:
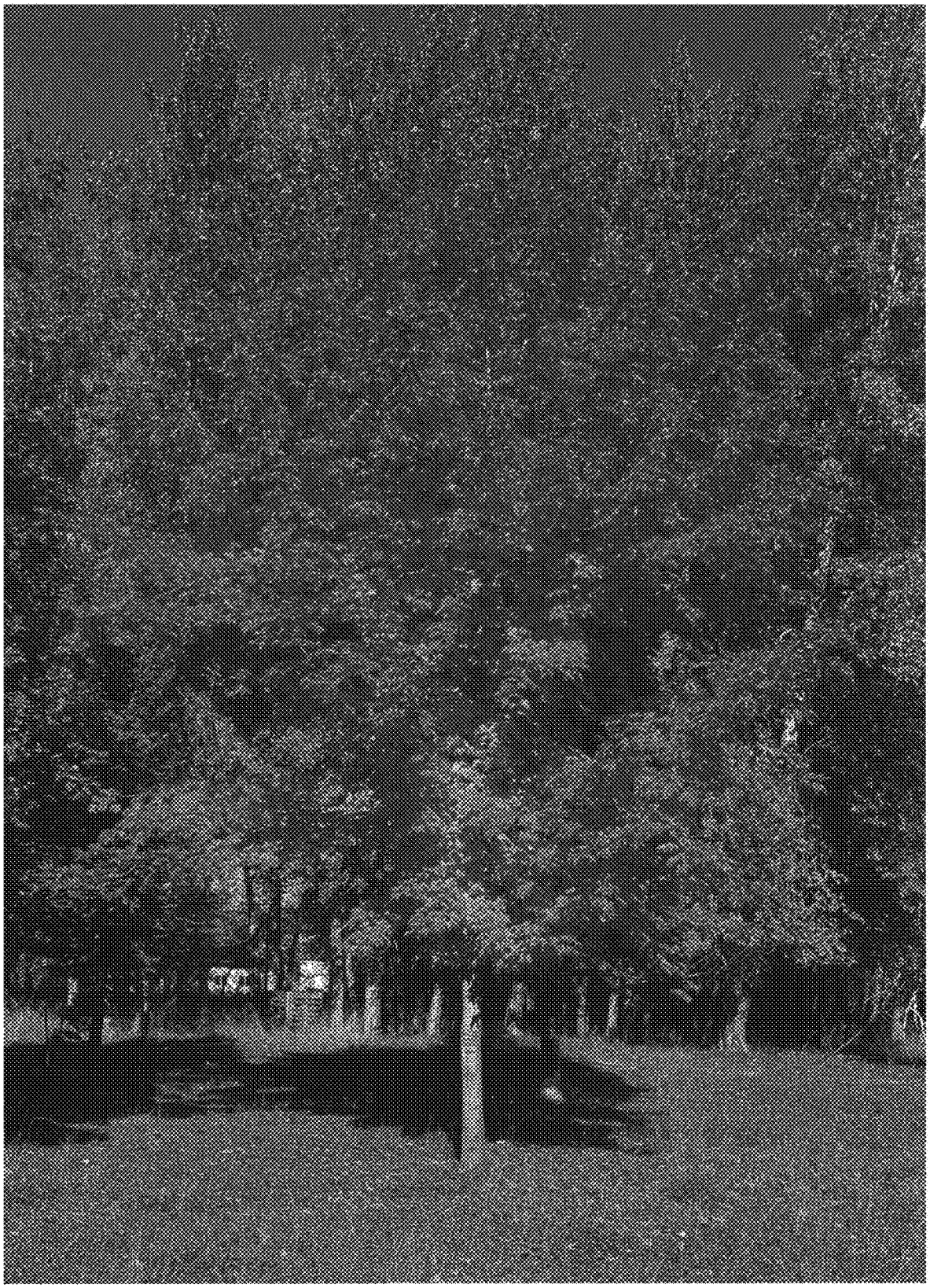
FIG. 1 Photograph of my sugar maple selection in September 2016, as grown on my farm in Bozeman, Mont., displaying brilliant red fall color and upright oval form. Age of tree in photo is 24 years.
Figure 2:
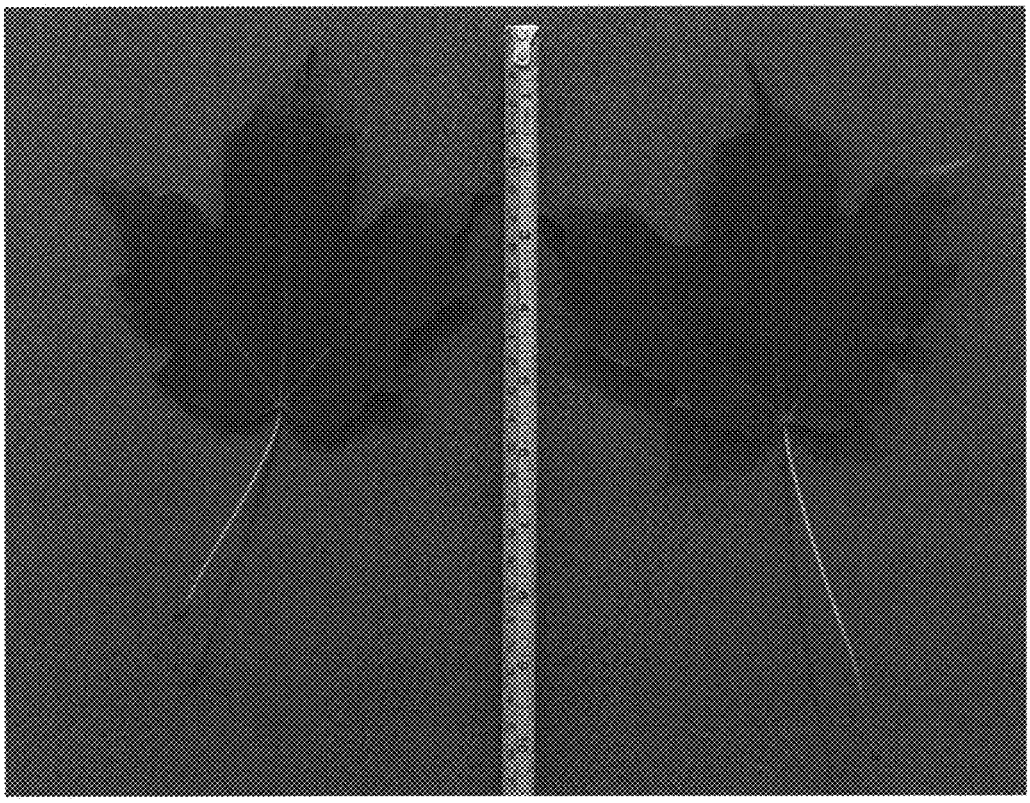
FIG. 2 Photograph of late summer 2020 leaves of my sugar maple with measurement, in Bozeman, Mont.
Figure 3:
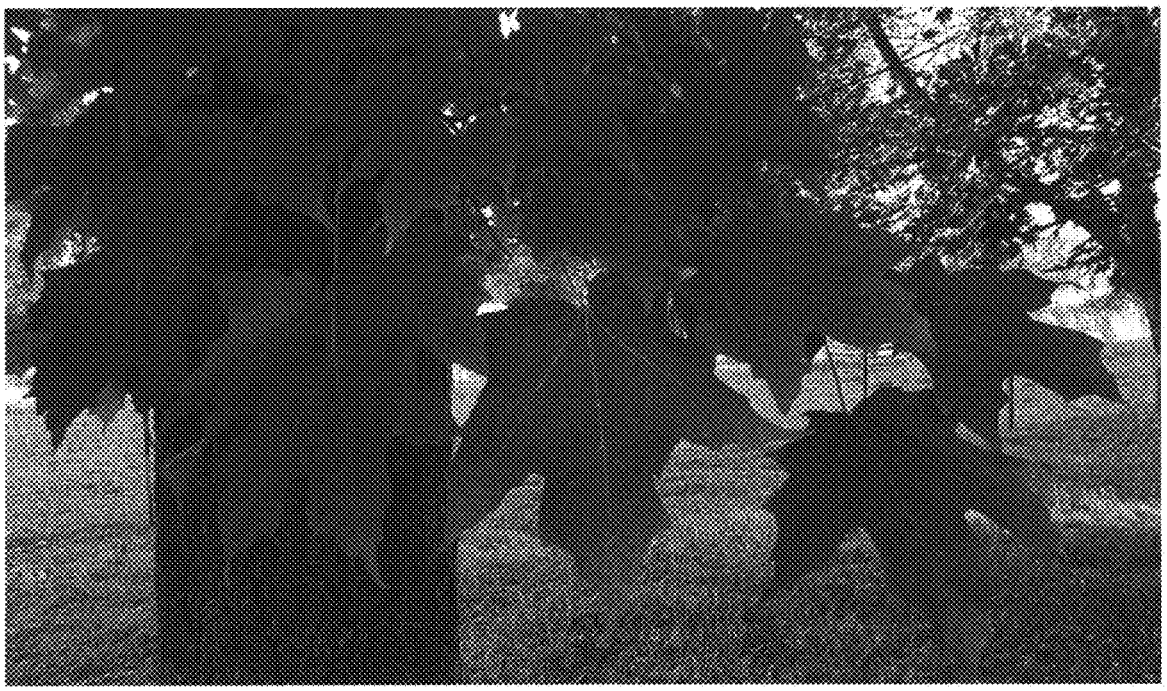
FIG. 3 Photograph of late summer 2020 leaves of my sugar maple in Bozeman, Mont.
Figure 4:
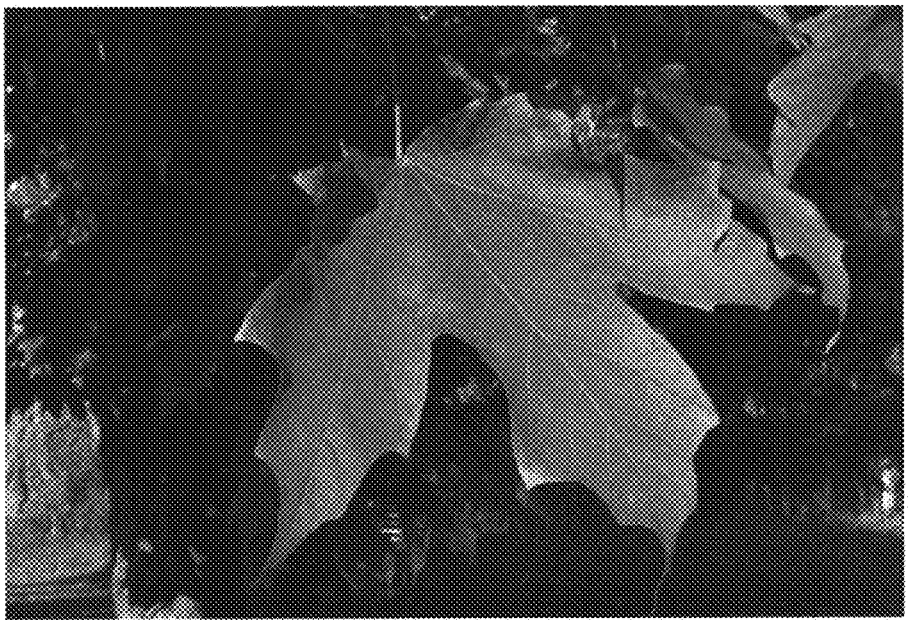
FIG. 4 Photograph of the leaves of my sugar maple transitioning directly from green to red in Sep. 24, 2020, in Bozeman, Mont.
Figure 5:
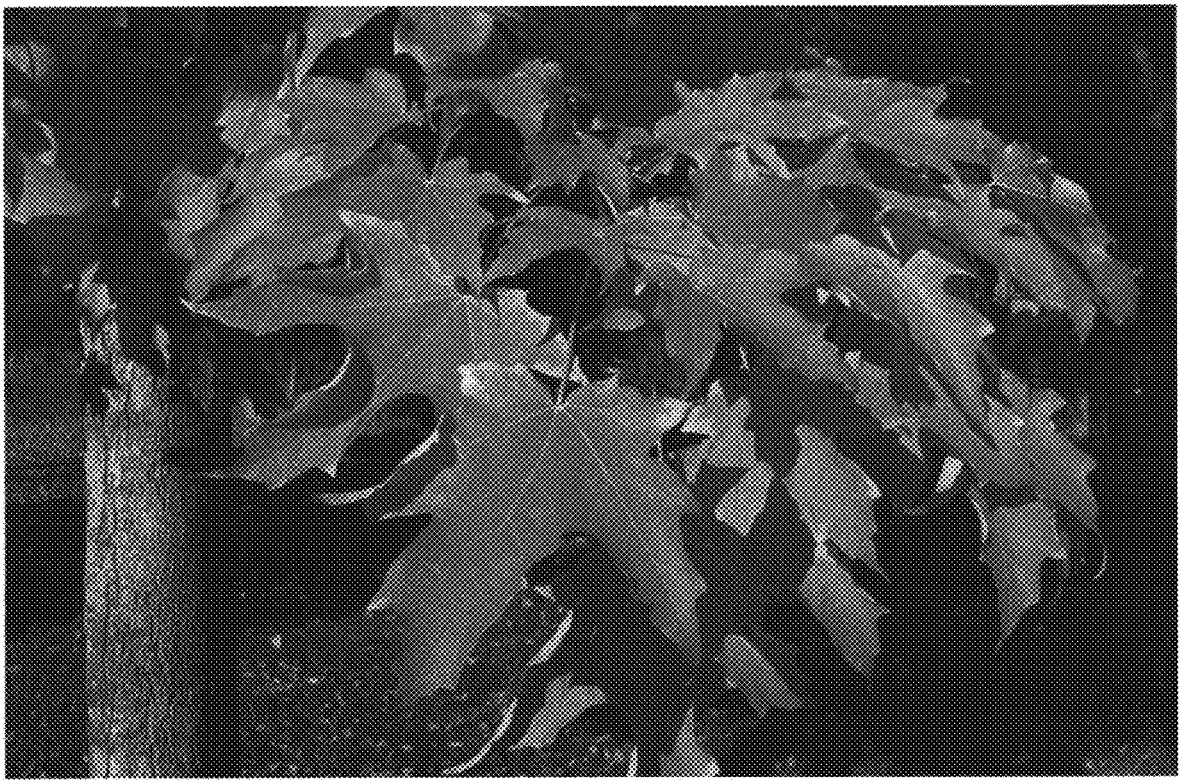
FIG. 5 Photograph of red fall leaf color of my sugar maple on Sep. 29, 2020 in Bozeman, Mont.
Figure 6:
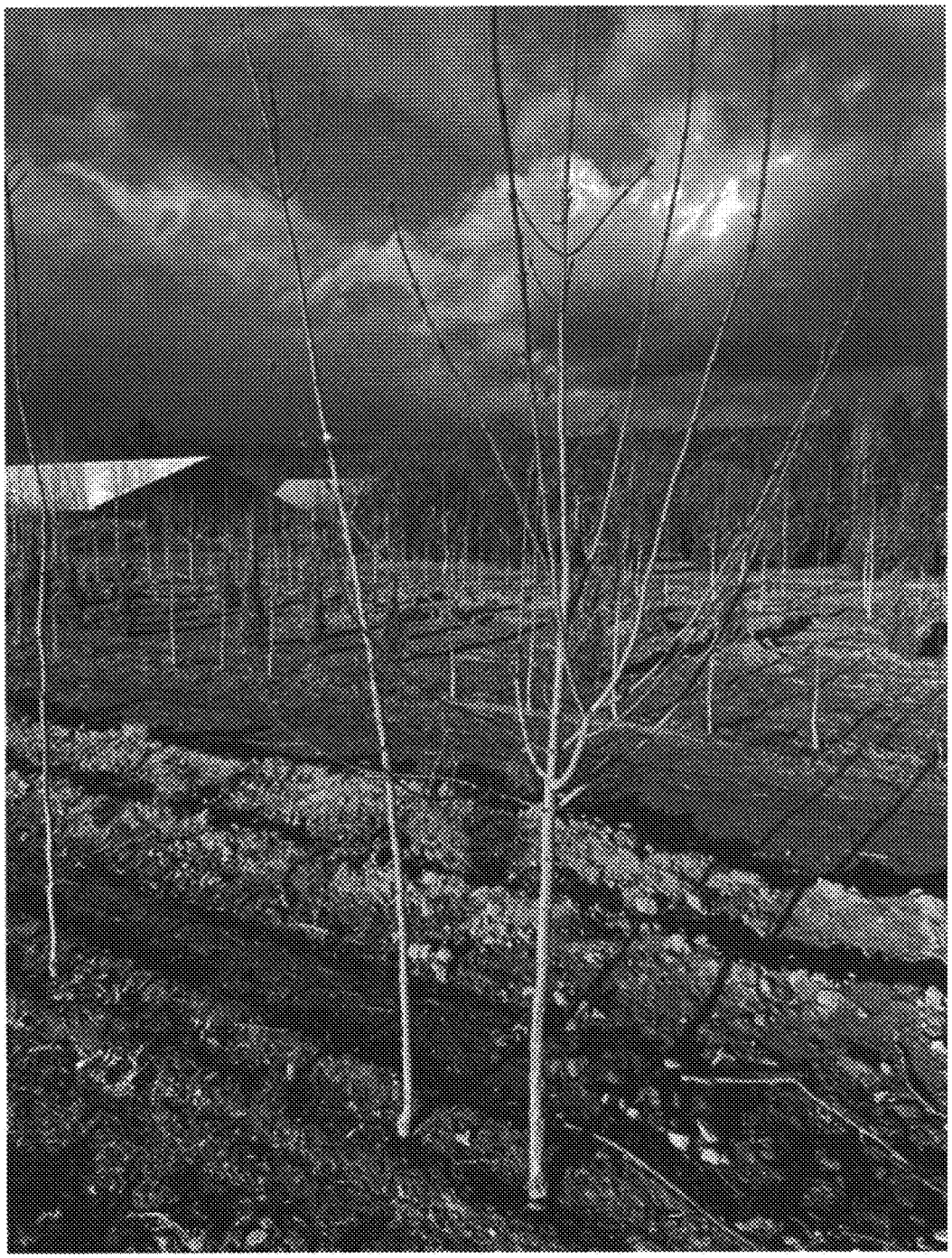
FIG. 6 Photograph of my asexually propagated sugar maple in winter dormancy at Apple Creek Propagators, Bonners Ferry, Id., April 2021.
Figure 7:
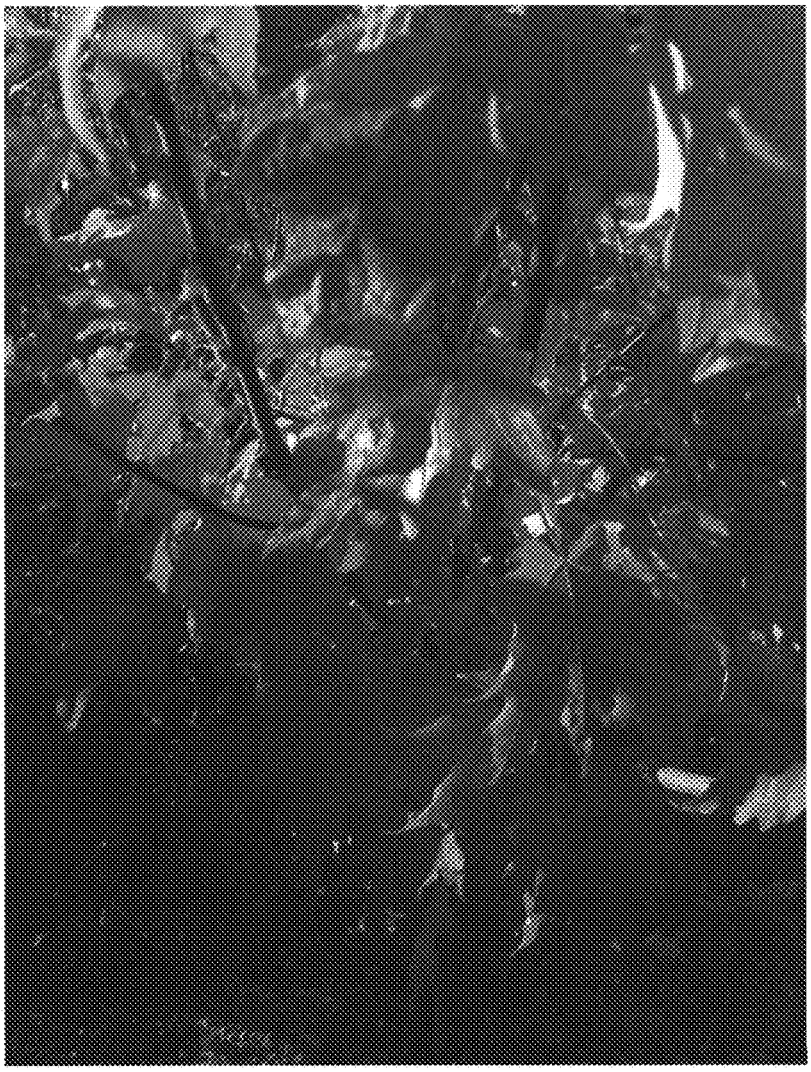
FIG. 7 Photograph of fall foliage on my asexually propagated sugar maple in production at Apple Creek Propagators, Bonners Ferry, Id., Oct. 11, 2020

My 'Gallatin' variety of *Acer saccharum* is currently growing on my farm in Bozeman, Mont. What follows is a detailed description of my new variety referencing color terminology from The Royal Horticultural Society (R.H.S.) Colour Chart published by The Royal Horticultural Society.

Parentage: Seed collected from 100+ year old sugar maples in Bozeman, Mont.'s historic Sunset Hills Cemetery.

Tree shape: In youth, upright and slightly columnar. At 15 years becoming oval in shape and by 25 years developing a broad, dense and spreading canopy.

Growth rate: Moderate to fast, 45 cm-60 cm per year in first 15 years, moderate 30 cm-40 cm per year after 20 years.

Bark: The young tree develops a smooth bark, grey (RHS 189D) in color. On my 29 year old tree, there is considerable irregularity to the bark; some areas remaining smooth while others exhibit a somewhat mottled and coarse texture and other regions deeply furrowed revealing a younger bark underneath. Bark becomes increasingly scaly with age and consistent with *Acer saccharum*. Color ranges from light grey (RHS 189D) in the smooth areas, to medium grey (RHS N189C) in the coarser, mottled areas, to darker grey (RHS N189B) in the very course, rough textured outer layer of bark. Rough areas of bark are deeply furrowed, to reveal an inner, younger bark of reddish brown color (RHS 177C).

Branching habit: Ascending branches from 35 to 45 degrees create a somewhat columnar tree in youth. Majority of major branches off the main leader are at 40 degrees, while smaller percentages of branches are 75 to 90 degrees from main leader.

Branches: Red brown (RHS 51B) new growth with prominent, white lenticels. Glabrous, lustrous. Three year old branches are grey (RHS 189D) slight vertical lines give some texture.

Branch lenticels: Most visible on one-year wood, vertical, 1 mm long, dense, white.

Branch internodes: Average 10 cm.

Buds: Terminal, 5-10 mm long, slightly pubescent at tip, generally the same as *Acer saccharum*.

FOLIAGE

Leaf size (sampling of typical leaves): Leaf (including petiole): 19 cm-31 cm in length and 13 cm-17 cm in width. Petiole: 9 cm-16 cm, light green (RHS 145B) in summer to fall's red-orange (RHS N30A). Side and middle lobes average 4.5 cm in width by 6 cm in length. Basal lobes average 1 cm in width by 1 cm in length. Leaf sinuses, between the center and side lobes, average 3 cm in depth and 1 cm in width at midpoint. Prominent, palmate veins, 1 mm, light green (RHS 154A).

Leaf shape (sampling of typical leaves): Opposite, simple, palmate, with 5 acuminate lobes, comprised of 2 prominent side lobes, an equally prominent middle lobe and 2 small basal lobes. Moderately narrow and deep sinuses between middle and side lobes. No serration. Truncate base. Side lobes consistently develop 2 additional points, the inner blunted while the outer is sharp. The center lobe presents two additional, moderately blunted points on each side. The middle and side lobes are typically equal in size, proportionate to leaf selected for measurement, while basal lobes are consistently and significantly smaller. Basal lobes regularly present an additional, small, blunted outer point.

Leaf color: Upper side: In summer, glabrous, medium to dark green (RHS 143A). Underside: In summer, slight pubescence, pale green (RHS 145A). Leaf color in fall: Transition from summer green to a very consistent and brilliant red (RHS N30A). Petiole light green (RHS 145B) in summer to fall's red-orange (RHS N30A).

Leaf emergence and leaf-fall: In Bozeman, Mont. (latitude approximately 45.5° N, elevation 4,800') leaf-out occurs between May 15 to May 20. Prime autumn color display occurs between September 25 and September 30, with leaf-fall complete by October 10. Leaf-fall for this variety consistently occurs two to three weeks ahead of other sugar maples grown on my farm, including Fall Fiesta® Sugar Maple and Green Mountain® Sugar Maple.

Crown spread: 6 meters to 7.5 meters at 29 years in age in Bozeman, Mont.

Fruit: The parent tree, at 29 years of age, has not yet produced flowers or samaras. This is typical of *Acer saccharum*, which produces flowers and fruit in later maturity. The tree has not been tapped and therefore sap yield volume is unknown.

Pest and disease resistance: No significant insect or disease damage in Bozeman, Mont. or Bonners Ferry, Id.

Winter hardiness: Grown and observed over 29 years in Bozeman, Mont. (USDA Zone 4b (−25° F. to −20° F.))

PROPAGATION AND PRODUCTION

In July 2017 I collected bud wood from my sugar maple, and at my direction, Apple Creek Propagators budded my selection onto one to two year old *Acer saccaharum* under stock growing in their field rows in Bonners Ferry, Id. Specializing in plants for harsh, inland, high-elevation climates, Apple Creek has asexually propagated several hundred more of my sugar maples over the past four years. The resulting trees have remained true to type, exhibiting exceptional hardiness in the fall of 2019 when a very early October freeze across the northern Rocky Mountain region damaged Fall Fiesta sugar maples growing in Apple Creek's nursery. In those same nursery fields, no tissue damage was observed in my sugar maples the following spring. In addition to the early dormancy characteristic, Apple Creek Propagators have observed the exceptional red fall leaf color of my sugar maple in their nursery, true to type with my tree in Bozeman, Mont.

What is claimed is:

1. A new and distinct variety of sugar maple tree as herein described and shown.

* * * * *